(12) United States Patent
Bochi

(10) Patent No.: US 7,488,173 B2
(45) Date of Patent: Feb. 10, 2009

(54) INSTRUMENT WITH PRESSURE SENSING CAPABILITIES

(76) Inventor: Antoine Bochi, 79 N. Broadway, White Plains, NY (US) 10603

( * ) Notice: Subject to any disclaimer, the term of this patent is extended or adjusted under 35 U.S.C. 154(b) by 102 days.

(21) Appl. No.: 11/359,757

(22) Filed: Feb. 22, 2006

(65) Prior Publication Data
US 2007/0196784 A1   Aug. 23, 2007

(51) Int. Cl.
*A61C 1/10* (2006.01)
(52) U.S. Cl. .................... 433/114; 433/98; 81/469; 81/479
(58) Field of Classification Search ............. 433/98, 433/99, 114; 81/469, 479, 478, 57.13, 57.29; 15/21.1, 22.1, 250.202
See application file for complete search history.

(56) References Cited

U.S. PATENT DOCUMENTS

| | | | |
|---|---|---|---|
| 1,242,115 A | | 10/1917 | Russell |
| 1,977,263 A | | 10/1934 | Campbell |
| 2,492,549 A | | 12/1949 | Barnes et al. |
| 2,928,174 A | | 3/1960 | White |
| 3,032,878 A | | 5/1962 | White |
| 3,106,732 A | * | 10/1963 | Dayton et al. .................. 15/28 |
| 3,235,222 A | * | 2/1966 | Nickell ........................ 251/3 |
| 3,449,831 A | | 6/1969 | Vandis |
| 3,520,063 A | * | 7/1970 | Rethwish et al. ............. 33/558 |
| 3,675,330 A | * | 7/1972 | Drapen et al. ................ 433/99 |
| 3,866,493 A | * | 2/1975 | Ringerud .................. 81/57.11 |
| 3,922,791 A | * | 12/1975 | Maxey et al. ............... 33/501 |
| 4,051,337 A | | 9/1977 | Warrin |
| 4,276,024 A | | 6/1981 | Warrin |
| 4,450,599 A | * | 5/1984 | Scheller et al. .............. 15/22.1 |
| 4,795,343 A | * | 1/1989 | Choisser .................... 433/116 |
| 5,071,418 A | | 12/1991 | Rosenbaum |
| 5,365,673 A | * | 11/1994 | Haimer et al. ............... 33/559 |
| 5,951,966 A | | 9/1999 | Wang |
| 6,258,088 B1 | | 7/2001 | Tzonev et al. |
| 6,375,459 B1 | * | 4/2002 | Kamen et al. ................ 433/80 |
| 6,585,512 B2 | | 7/2003 | Van Hale |
| 6,929,476 B2 | | 8/2005 | Katsuda et al. |
| 2004/0164972 A1 | * | 8/2004 | Carl .......................... 345/179 |
| 2005/0042572 A1 | | 2/2005 | Katsuda et al. |

FOREIGN PATENT DOCUMENTS

DE     2906892 A  *  9/1980

OTHER PUBLICATIONS

English Translation of Foreign Patent DE 2906892; Translated by Schreiber Translation, Inc.*

* cited by examiner

*Primary Examiner*—John J Wilson
*Assistant Examiner*—Hao D Mai
(74) *Attorney, Agent, or Firm*—Arthur Jacob

(57) ABSTRACT

A hand held instrument for carrying out some function on a work piece. The instrument is a handpiece that is held by the user and includes a working element at the distal end of the handpiece for working on the work piece. There is a source of power that activates the working element by providing power thereto in various forms. There is also a pressure sensor that senses the pressure between the working element and the handpiece. In one embodiment that pressure sensor senses a predetermined pressure in order to couple the power source to the working element for activating the working element. In another embodiment, the pressure sensor senses a reduction in pressure between the working element and the handpiece to illuminate an indicator light.

16 Claims, 1 Drawing Sheet

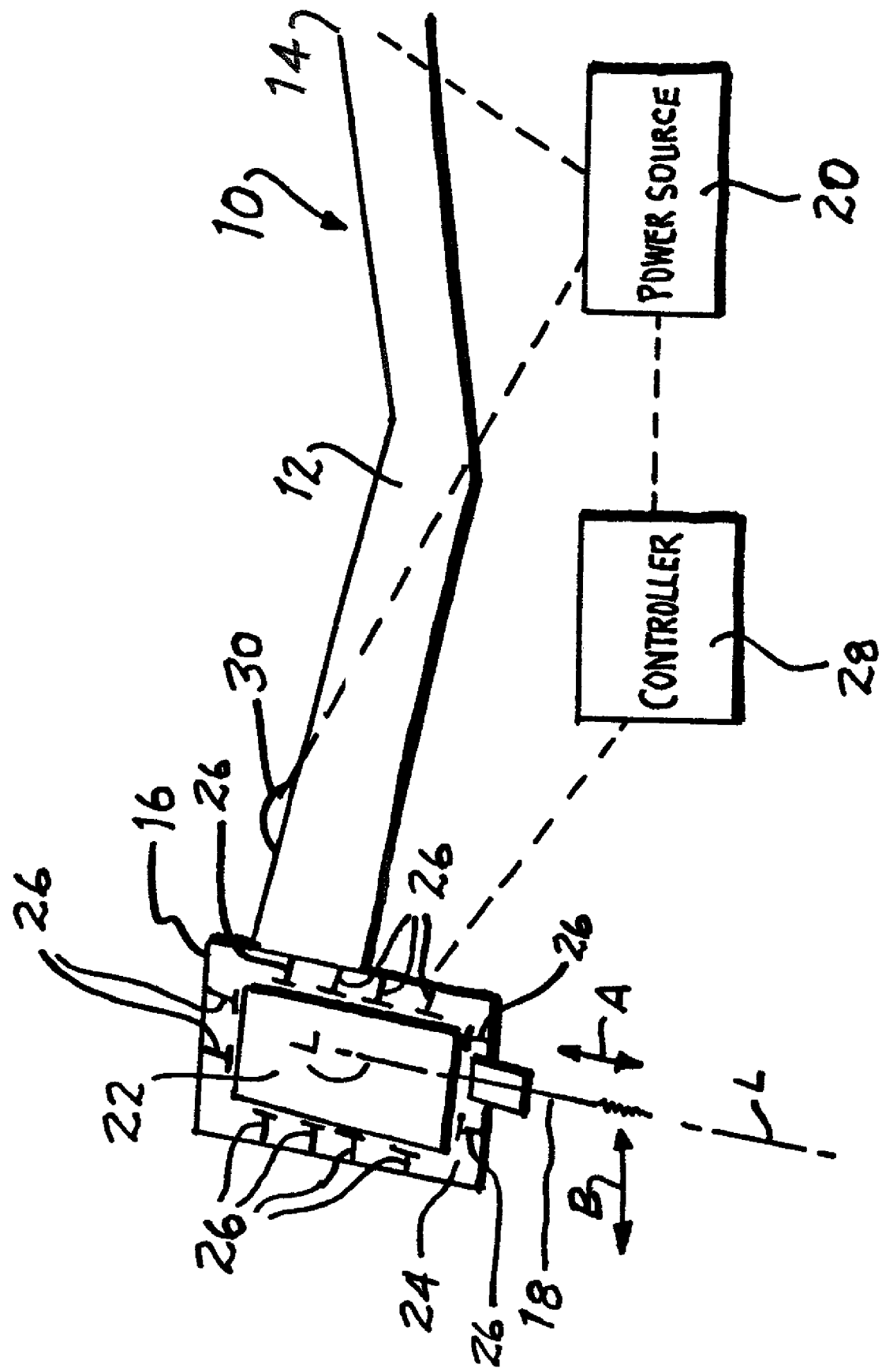

INSTRUMENT WITH PRESSURE SENSING CAPABILITIES

BACKGROUND

The present invention relates to a hand held instrument having a working element, such as a drill bit, to carry out some function on a work piece and more particularly, to a hand held instrument having a pressure sensor to determine the pressure between the working element and the hand held instrument.

There are numerous differing types of hand held instruments that are in use or have been proposed to apply a working element to some work piece. Those instruments can include a normal hand drill for use by an individual or one of many hand held devices that are used in the dental field including but not limited to, a dental drill, a Cavitron instrument for cleaning teeth and a dental laser.

In any case, the instrument is a hand held instrument and there is some power source that provides a power to operate a working element that is located at the distal end of the instrument. The source of power may be a source of rotational power, as is used with a dental drill, an electrical signal as is used with a vibrating tooth cleaning device, a pressurized source of gas such as is used in a turbine powered dental drill or other source of power.

In such hand held instruments, there is also normally some switching device located in close proximity to the user that can be manually operated by the user in order to apply the source of power to activate the working element to carry out some procedure. Such switching devices can include devices that are, for example, foot operated switches or some switching device that is located on the hand held instrument itself. In such present switching devices, however, it is necessary for the user to take some deliberate, manual action to activate a switch to connect the source of power to the working element to carry out the function of the working element of the hand held instrument. The user is, at the time of the switch activation, concentrating on the target for the working element and it can be distracting to require some physical activation of a switching device with the hand or foot of the user in order to activate the working element.

Accordingly, it would be advantageous to have a switching system or device that can activate the working element automatically without the need for the user to actually push or otherwise take some potentially distracting action to operate a switching device to commenced the action of the working element so that the user can more fully concentrate on the location and use of the working element as it is applied to the target work piece.

In addition, there is another feature of present hand held instruments that is currently lacking and which could enhance the use of such instruments to the user. Using the example of a dental drill, in the drilling of a patient's tooth to carry out a procedure in filling a cavity, the user normally engages the working element of the dental instrument to the tooth enamel and moves the working element inwardly with respect to the tooth in working on the cavity. There is a point in the procedure where the drill bit passes through the hard outer enamel of the tooth and enters the softer material that comprises the pulp cavity of the tooth and, at that point, there is a lessening of the pressure on the working element since the drill is now entering the less dense portion of the tooth i.e. the cavity.

While the user can normally feel that transition from the harder material of the enamel to the softer material, it would be advantageous to have some visible or audible indication that would alert the user that the drill bit has passed through the hard enamel and has reached the less dense material of the pulp cavity.

SUMMARY OF THE INVENTION

Accordingly, the present invention relates to a hand held instrument for applying a working element to a work piece to carry out some procedure on that work piece. The hand held instrument comprises a handpiece that can be easily manipulated by the user and which has a working element that is used to carry out some procedure on a work piece.

The description of an exemplary embodiment in this specification is directed to an embodiment where the instrument is a dental instrument, such as a dental drill, and thus the working element is a drill bit for drilling into the tooth of the patient, however, it will be understood that the present invention pertains to other hand held instruments and other working elements, that is, the present invention can be applicable to a Cavitron instrument used for prophylaxes, a dental laser as well as for various procedures and instruments used in carrying out implant or cosmetic dentistry. In addition, the present invention can be applied to an otherwise conventional hand instruments used in home or industrial applications.

In any event, the hand held instrument of the present invention includes a source of energy or power that is provided to activate the working element and, as explained, that source may be a variety of sources including a source of rotational motion or power as would be used with a drill including, but not limited to, a small motor located in the hand piece, a centrally located motor with belts that transmit the rotary motion from the motor to the handpiece. The source of power or energy can also be a source of pressurized gas, such as air, to power pneumatic hand held instruments including turbine powered drills that are used in dental instruments.

A further source of power or energy may also be simply a source of electrical energy and which may be used to power some mechanism located in the hand held instrument including a vibrating member used for cleaning the teeth, such as a Cavitron instrument.

As a further element of the present invention, there is a pressure sensor that senses the pressure between the working element and the handpiece. Again, the present invention may utilize any of one of a variety of differing pressure sensors that measure the magnitude of the pressure between the working element and the handpiece and the working element may be a variety of devices indicated above.

The pressure information from the pressure sensor can be used in more than one manner. For example the pressure sensor may determine the existence of a predetermined pressure between the working element and the handpiece so as to activate the working element. In the case of a dental drill, the working element is a drill bit and the pressure is thus sensed between the drill bit and the handpiece such as when the dentist has pressed the drill bit against a tooth to be drilled. That contact with the tooth thus creates a pressure that is sensed between the drill bit and the handpiece and, when that pressure reaches a predetermined plateau, the power source is applied to the working element to activate that working element. In the case of a dental drill, the power source is a source of rotational motion and which therefore commences the rotation of the drill bit to carry out the drilling of the tooth.

As such, to initiate the dental drill, the dentist need only contact the drill bit with the tooth with sufficient pressure such that the pressure sensor can cause the power source to rotate the drill bit and there is no need for the user to use a foot pedal or other switching device that can detract the attention of the dentist. Thus, the hand held dental instrument would automatically commence the rotation of the working element upon sufficient contact with a tooth by the working element.

In connection with the aforementioned activation of the rotational motion source there may also be an indicator light located on the handpiece or other location convenient to the user, to indicate that the source of rotational motion has been activated and thus the working element is operational.

As another use of the pressure sensor of the present invention, in a procedure to fill a cavity, the dentist normally drills through the hard enamel of the tooth to reach the cavity itself. As such when the drill bit has reached the pulp cavity, lying beneath the enamel of the tooth, the drill undergoes a transition from the hard enamel of the tooth to a softer material of the pulp cavity. As such, there is a reduction of the pressure between the working element and the handpiece.

That transition point is informative to the user and therefore with the present invention there may be an indicator that alerts the user to the transition between the hard enamel of the tooth and the less dense material within the pulp cavity. That indicator can provide a visual or audible alert, or both. In either case, the user is notified clearly that the drill has passed through the hard enamel of the tooth and into the pulp cavity by means of the pressure sensor sensing a reduction in pressure between the working element and the handpiece.

Again while preferred for use with a dental instrument, it can be seen that the visual or audible alert advising the user of a reduction in pressure between the working element and the handpiece can be of use with a utility drill so that the user will immediately become alerted when the drill bit has passed through the work piece, such as a piece of wood, wall board of other material so that the drill can be withdrawn.

These and other features and advantages of the present invention will become more readily apparent during the following detailed description taken in conjunction with the drawings herein.

BRIEF DESCRIPTION OF THE DRAWINGS

The drawing is a schematic view of a hand held instrument constructed in accordance with the present invention.

DETAILED DESCRIPTION OF THE INVENTION

Referring now to the drawing, there is shown a schematic view of a hand held instrument 10 constructed in accordance with the present invention. As can be seen, the hand held instrument 10 comprises a handpiece 12 having a proximal end 14 and a distal end 16.

At the distal end 16, there is a working element 18 that is used to carry out some action by the use of the hand held instrument 10. In the case of a dental drill, which is the embodiment illustrated in the FIGURE, the working element is, of course, a drill bit. In the case of other hand held instruments, the working element may be a variety of other devices, including a laser element in the case of a dental laser, a vibrating element in the case of a Cavitron instrument, or other element.

There is also a power source 20 that supplies some type of power or energy to the working element 18 to make it operational. Again the power source 20 can be a variety of sources and, in the embodiment illustrated in the drawing, the power source 20 can be a source of rotational movement that is ultimately transmitted to the working element 18 to rotate the working element 18 in order for the dentist to drill the tooth. Conventionally, that rotational movement can be provided by an electric motor located remotely from the hand held instrument 10 and the rotational movement transmitted to the working element 18 by a belt or pulley system.

As alternatives, the source of power may be a source of compressed air that can be transmitted to the working element 18 where there is a turbine that operates the working element 18 or the source of power can simply be a source of electricity that can be supplied to the working element 18 for example where the working element 18 is a device such as a laser element, a vibrating element that is used for cleaning teeth or even a small electric motor located at the distal end 16 of the handpiece 12.

In any event, the power source 20 provides the power or energy to cause the working element 18 to carry out its function, whether that function is drilling, cutting, cleaning or some other function. In a conventional hand held instrument, there is normally a switch, be it electrical or pneumatic, that connects the power source 20 to the working element 18, however, in the present invention there is a pressure sensor that senses the pressure between the working element and the hand piece that can be used to control the application of the power source 20 to the working element 18 and which allows the user to concentrate on the use of the hand held instrument 10 and not be distracted by the need to manually activate some switch to energize the working element.

Accordingly, while there may be many differing means and devices that can be employed to sense the pressure between the working element 18 and the handpiece 12, an exemplary suitable sensor is illustrated in the drawing. As can be seen, the working element 18 is retained by a housing 22 located at and within an internal chamber 24 located at the distal end 16 of the handpiece 12.

There are a plurality of position sensors 26 that are located within the distal end 16 of the handpiece 12 and which contact the housing 22 so as to sense the position or movement of the housing 22, that is, as the housing 22 moves, the sensors 26 detect that movement. Since the housing 22 supports the working element 18, it can be seen that the normal movement between the housing 22 and the working element 18, as would be caused by some pressure on the working element 18 with respect to the housing 22, is sensed by the position sensors 26. As such, the position sensors 26 effectively provide a means of sensing the pressure between the working element 18 and the handpiece 12.

The working element 18 in the drawing is shown as a dental drill bit and which has a longitudinal axis L and, by the employment of a plurality of position sensors 26 that surround the perimeter of the housing 22, including the upper and lower surface thereof, the position sensors 26 can sense when the housing, i.e. the working element 18 moves along its longitudinal axis resulting in a force exerted on the working element 18 in the direction of the double arrow A or if the housing 22 tilts as would be the result of a radial force exerted on the working element 18 in the direction of the double arrow B. Therefore the present pressure sensor that senses the pressure between the working element 18 and the handpiece 12 can sense that pressure whether exerted axially along the longitudinal axis of the working element 18 or in a radial direction to the working element 18.

There is also a controller 28 that can be a microprocessor that receives the individual signals from the position sensors 26 so as to interpret those signals in order to take some action.

One of the actions that can be taken by the controller 28 is to cause the power source 20 to activate the working element 18 upon the sensing of a certain pressure by the pressure sensor i.e sensing the pressure between the working element 18 and the handpiece 12. As an example, in the exemplary embodiment shown in the FIGURE, the hand held instrument 10 is a dental drill and thus, the controller 28 can provide the rotational movement to the drill bit upon the sensing of a predetermined pressure between the working element 18 and the handpiece 12 such as would be created by the dentist touching a tooth with the working element 18. As such, the drill bit will automatically commence rotating when the dentist simply touches the working element, i.e. the drill bit to the surface of the tooth and the dentist thereby has no need to be distracted by trying to activate some manual switch to commence the drill operation.

In the embodiment where the hand held instrument is a dental drill, the dentist need only contact the surface of the tooth to activate the working element, that is, to start the rotation of the drill bit to carry out the procedure on the tooth and there is no need for a foot switch or other manually activated switch controlled by the dentist. Obviously, when the pressure is lessened such as where the dentist withdraws the dental drill from the tooth or somehow eases off on the application of the drill to the tooth, the rotational power can be automatically terminated by the controller 28 since the pressure then being sensed by the pressure sensor would be below the predetermined pressure.

The controller 28 carries out the same function when the hand held instrument is other than a dental drill. For example, if the hand held instrument is a dental laser, the working element may be the end of the laser unit and when that end is moved inwardly, with respect to the laser handpiece, the controller 28 can connect a source of electrical energy to activate the laser.

In a similar manner, the hand held instrument may be a Cavitron prophylaxis instrument where there is a vibrating working element at the distal end of the handpiece and, again, the working element 18 contacts the tooth or gum area in order to be sensed by the controller 28 and connect a source of electrical power to activate the vibrating element for cleaning of the patient's teeth.

With respect to non-dental hand held instruments, such as a utility drill, again the rotation of the drill bit can be commenced by the contact of the drill bit with a work piece, such as a piece of wood, and the controller 28 can sense that pressure between the drill bit and the handpiece in order to start the rotation of that drill bit. When the pressure is abated, the controller can terminate further rotation of the drill bit.

As can also be seen in the drawing, there is an indicator light 30 on the handpiece 12 that is basically located on the rear surface of the hand held instrument 10 and in a position to be visually perceived by the user. That indicator light 30 can be energized by the controller 28 upon the activation of the working element so that the user can know that the hand held instrument 10 is in operation.

As a further embodiment involving the indicator light 30, the indicator light 30 can be activated by the controller 28 when there is a lessening of pressure between the working element 18 and the handpiece 12, that is, the indicator light 30 may be activated when there is a reduction of pressure exerted on the working element 18.

With this embodiment, the indicator light 30 provides an indication that the pressure on the working element 18 has actually eased up. For example, if the hand held instrument 10 is a dental drill and the working element is a drill bit, it is useful information to the user to know when the drill bit has penetrated the outer, hard enamel of the tooth and entered the softer interior of the tooth. With the present invention, as the drill bit passes through the enamel, the resultant transition into the softer material of the pulp cavity inherently reduces the pressure between the working element 18 and the handpiece 12. Thus, the controller 28 can sense that reduction in pressure and illuminate the indicator light 30 to make it clear to the user that the working element has entered a less dense area. While only one indicator light 30 is shown in the drawing, it can be seen that there may be two indicator lights, one for the purpose of indicating that the working element is energized and the other to inform the user of the aforedescribed decrease in pressure between the working element and the handpiece.

With a utility drill, such an activation of the indicator light 30 resulting from a reduction of pressure between the working drill bit and the hand held instrument can inform the user that the drill bit has, for example, passed through a dense material and has entered a less dense area such as when the drill bit has passed through wood or wallboard and has entered a void area in a wall.

Those skilled in the art will readily recognize numerous adaptations and modifications which can be made to the hand held instrument of the present invention which will result in an improvement in the instrument or its use, yet all of which will fall within the scope and spirit of the present invention as defined in the following claims. Accordingly, the invention is to be limited only by the following claims and their equivalents.

What is claimed is:

1. A hand held instrument comprising:
a handpiece having a distal end, and a chamber at the distal end of the handpiece;
a housing extending within the chamber;
a working element to be applied to an object, the working element being carried by the housing and extending along a longitudinal axis;
a power source for actuating the working element;
a pressure sensor arrangement within the chamber between the housing and the handpiece in place for sensing pressure between the working element and the handpiece, the pressure sensor arrangement being arranged relative to the housing and the working element for sensing pressure between the working element and the handpiece in axial directions along the longitudinal axis and in radial directions transverse to the longitudinal axis; and
a controller for activating the power source to actuate the working element, the controller being responsive to the pressure sensor arrangement for activating the power source to actuate the working element in response to forces upon the working element in the axial directions along the longitudinal axis and in the radial directions transverse to the longitudinal axis such that forces exerted upon the working element in either one of an axial direction along the longitudinal axis and a radial direction transverse to the longitudinal axis will activate the power source to actuate the working element, and will continuously activate the power source to actuate the working element while such forces are exerted upon the working element.

2. A hand held instrument as defined in claim 1 wherein the power source is a source of rotational power.

3. A hand held instrument as defined in claim 2 wherein the working element is a drill bit.

4. A hand held instrument as defined in claim 3 wherein the hand held instrument is a dental instrument.

5. A hand held instrument as defined in claim 1 wherein the power source is a source of pressurized air.

6. A hand held instrument as defined in claim 5 wherein the hand held instrument is a dental instrument and the working element is a turbine operated rotary tool.

7. A hand held instrument as defined in claim 1 wherein the power source is a source of electrical power.

8. The hand held instrument as defined in claim 1 wherein the hand held instrument is a dental instrument and the predetermined pressure is sensed when the working element contacts a tooth of a patient.

9. The hand held instrument as defined in claim 8 wherein an indicator light is illuminated to alert a user that the power source has been activated by the sensing of the predetermined pressure.

10. The hand held instrument as defined in claim 1 wherein a predetermined decrease in pressure sensed by the pressure sensor illuminates an indicator light located on the hand held instrument.

11. A method of using a hand held instrument for application to a work piece comprising the steps of:
    providing a handpiece having a working element for application to a work piece, the working element extending along a longitudinal axis,
    providing a source of energy to activate the working element,
    sensing pressure between the handpiece and the working element in either one of an axial direction along the longitudinal axis and a radial direction transverse to the longitudinal axis as the hand held instrument is applied to a work piece, and
    activating the source of energy in response to sensing a pressure in either one of the axial direction and the radial direction to actuate the working element in response to forces upon the wording element in the axial direction along the longitudinal axis and in the radial direction transverse to the longitudinal axis, and continously activating the power source to actuate the working element while such forces are exerted upon the working element.

12. The method as defined in claim 11 wherein the step of providing a source of energy comprises providing a source of rotational movement that rotates the working element upon the sensing of a predetermined pressure between the handpiece and the working element.

13. The method as defined in claim 12 wherein the hand held instrument is a dental instrument and the step of sensing the pressure comprises sensing the pressure resulting from the working element contacting a tooth of a patient.

14. The method as defined in claim 11 wherein the step of providing a source of energy comprises providing a source of electrical power.

15. The method as defined in claim 12 further including the step of activating an indicator light when the source of rotational movement has been activated.

16. The method as defined in claim 11 further including the step of activating an indicator light when the step of sensing the pressure results in sensing a reduction in pressure between the hand piece and the working element.

* * * * *